United States Patent [19]

Ott

[11] 4,369,176
[45] Jan. 18, 1983

[54] METHOD OF ATTRACTING AND KILLING INSECTS

[75] Inventor: Jerry E. Ott, Phoenix, Ariz.

[73] Assignee: Farnam Livestock Equipment and Insecticides, Inc., Phoenix, Ariz.

[21] Appl. No.: 962,231

[22] Filed: Nov. 20, 1978

[51] Int. Cl.³ .................... A01N 25/00; A01N 47/10; A01N 57/00

[52] U.S. Cl. .................... 424/84; 424/217; 424/219; 424/225; 424/300; 424/305

[58] Field of Search .............................. 424/219, 84

[56] References Cited

FOREIGN PATENT DOCUMENTS 111917 7/1962 Pakistan ........................... 424/219

Primary Examiner—Allen J. Robinson
Attorney, Agent, or Firm—William H. Drummond

[57] ABSTRACT

Insects are attracted to and killed by a poison bait which includes an attractant-producing composition. The attractant-producing composition includes a sugar, a spore-producing bacteria of the genera Bacillus, and a carrier for the sugar and the bacteria.

1 Claim, No Drawings

METHOD OF ATTRACTING AND KILLING INSECTS

This invention relates to methods of attracting and killing insects.

Poisonous baits for insects are well known. For example, appropriate systemic or contact insecticides are conventionally mixed with sugar and sugar-containing compositions and the resultant mixture proves quite highly effective in killing insects, such as common houseflies and the like. Specific examples of illustrative insecticides which are effectively employed in such compositions are:

Dimethyl-2,2 dichlorovinyl phosphate
Dimethyl-2,2 trichloro-1-hydroxyethyl phosphorate
S-methyl-N (methylcarbamoyl) oxy-thioacetimidate
2-(1-methylethoxyphenyl) phenyl methylocarbamate
0,0-dimethyl-0-(2,4,5-trichlorophenyl) phosphorothioate
(3-phenoxyphenol) methyl (±cis trans-3-(2-dichloroethenyl)—2,2-dimethylcyclopropanecarboxylate While such compositions function effectively to kill insects which actually eat or contact the posion bait, their effectiveness is reduced by reason of the fact that such baits do not ordinarily "attract" insects. Rather, it is necessary to spread the bait in the locus to which the insects are normally otherwise attracted, i.e., manure piles, garbage dumps, cool bare floors, and the like.

It would be advantageous to provide a method for attracting flies and other insects to desired preselected locations. It would also be advantageous and desirable to provide methods which utilize in situ formation of an insect to provide an attractant-producing poison bait composition which steadily emits an effective quantity of insect attractant over a prolonged time period, a so-called "timed release" effect.

These and other, further and more specific objects and advantages of the invention will become apparent from the following detailed description thereof.

I have now discovered methods of attracting and killing insects utilizing such attractants and insecticide compositions.

According to the invention, I provide a method of attracting insects to a preselected area including the step of disposing in said preselected area an effective quantity of an insect attractant composition comprising a sugar and spore-producing bacteria of the genera Bacillus for biologically degrading the sugar to form an insect attractant, and a carrier for the sugar, insecticide and bacteria.

In the preferred embodiment of the invention, the attractant-precursor compound is a sugar or sugar derivatives, especially sucrose.

Illustratively, and according to the presently preferred embodiment of the invention, when one employs sucrose as the precursor compound, it is effectively and efficiently degraded by bacteria of the family Bacillaceae, of the genera Bacillus, spore-producing bacteria which secrete enzymes which in turn produce fermentation of sugars.

A carrier is provided for the sugar and the bacteria. The carrier serves the dual function of providing a convenient way to handle the insect attractant composition while simultaneously maintaining the bacteria in biological contact with the sugar. The exact nature of the carrier is not highly critical. For ease of formulation and handling, the carrier is preferably porous and granular. Specific preferred examples of such materials are ground corncobs, coarse sawdust or comminutes expanded polystyrene, sand, etc.

The insect attractant composition described above is conveniently prepared by simple physical mixing of the sugar, the bacteria and the carrier. As will be appreciated by those skilled in the art, certain naturally occurring carrier materials, such as ground corncobs, may already contain the desired Bacillus bacteria. The carrier may be easily and conveniently innoculated with the bacteria if the carrier material does not already contain it or if the concentration thereof is too low. The sugar is applied to the carrier by any convenient technique such as, for example, spraying or soaking the carrier with a solution of a melt of the sugar.

The following example is presented to identify the presently preferred embodiment of the invention and illustrate the preferred practice thereof sufficiently that those skilled in the art can understand and practice the invention without undue experimentation.

A Bacillus culture is prepared by washing 10 lbs. of ground corncobs with distilled water and filtering the wash liquor through a microporous filter. The filtrate is discarded and the residue remaining on the microporous filter is cultured in a 500 ml. flash with nutrient agar, according to art-recognized techniques.

400 lbs. of sugar are dissolved in 100 gallons of water to form a supersaturated syrup. 500 ml. of the Bacillus cereus culture, estimated to contain approximately 12 million spores, prepared as described above are mixed with the sugar syrup. The innoculated syrup is then mixed with the sugar syrup. The innoculated syrup is then mixed with 500 lbs. of ground corncobs (number 1014 grit). The innoculated corncob grit is stored in sealed containers for a period of 3 months at 80° F. to initiate the fermentation reaction.

After fermentation of the innoculated corncobs as described above, 10 lbs. of dichlorovinyl dimethyl phosphate ("Vapona") are mixed with the fermented corncobs to form the final insecticidal attractant composition.

The attractant composition is spread on the ground in areas remote from animal or human habitations to attract the insects away from the habitations and kill them at the remote location.

Having described my invention in such clear, full and concise terms as to enable those skilled in the art to understand and practice it, and having identified the presently preferred embodiments thereof.

I claim:

1. A method for attracting insects to a remote location and killing said insects at said location, said method comprising:
   (a) forming an insecticidal bait by mixing
      (i) a sugar,
      (ii) sufficient spore-producing bacteria of the genera Bacillus to cause fermentation of said sugar with the concomitant production of insect-attractant values,
      (iii) a minor amount of an insectide in sufficient quantity to kill insects attracted to said bait, and
      (iv) a granular carrier in sufficient amount to carry said sugar, bacteria and insecticide; and
   (b) spreading a quantity of said bait in said remote location in an amount sufficient to attract insects to said location and to kill said insects in said location.

* * * * *